(12) United States Patent
Sun et al.

(10) Patent No.: US 11,817,215 B2
(45) Date of Patent: Nov. 14, 2023

(54) ARTIFICIAL INTELLIGENCE CLOUD DIAGNOSIS PLATFORM

(71) Applicant: WUHAN LANDING INTELLIGENCE MEDICAL CO., LTD., Hubei (CN)

(72) Inventors: Xiaorong Sun, Hubei (CN); Baochuan Pang, Hubei (CN); Feilong Zhang, Hubei (CN); Dehua Cao, Hubei (CN); Sai Liu, Hubei (CN)

(73) Assignee: WUHAN LANDING INTELLIGENCE MEDICAL CO., LTD.

( * ) Notice: Subject to any disclaimer, the term of this patent is extended or adjusted under 35 U.S.C. 154(b) by 108 days.

(21) Appl. No.: 17/297,411

(22) PCT Filed: Oct. 5, 2020

(86) PCT No.: PCT/CN2020/119812
§ 371 (c)(1),
(2) Date: May 26, 2021

(87) PCT Pub. No.: WO2021/068857
PCT Pub. Date: Apr. 15, 2021

(65) Prior Publication Data
US 2022/0230748 A1    Jul. 21, 2022

(30) Foreign Application Priority Data

Oct. 11, 2019 (CN) .......................... 201910984425.7

(51) Int. Cl.
*G16H 50/20* (2018.01)
*G16H 40/67* (2018.01)
(Continued)

(52) U.S. Cl.
CPC .......... *G16H 50/20* (2018.01); *G06T 7/0012* (2013.01); *G06T 7/136* (2017.01); *G16H 15/00* (2018.01); *G16H 30/40* (2018.01); *G06T 2207/10061* (2013.01); *G06T 2207/20081* (2013.01); *G06T 2207/30024* (2013.01)

(58) Field of Classification Search
None
See application file for complete search history.

(56) References Cited

U.S. PATENT DOCUMENTS

| 2014/0272768 A1* | 9/2014 | Curry ................. A46B 15/0055 433/29 |
| 2018/0008159 A1* | 1/2018 | Wang ..................... G16H 50/20 |
| 2021/0082570 A1* | 3/2021 | Zhalyalov .............. G16H 40/67 |

FOREIGN PATENT DOCUMENTS

| CN | 110675946 A | * | 1/2020 |
| CN | 111863235 A | * | 10/2020 |

\* cited by examiner

*Primary Examiner* — Mohammed Rachedine

(57) ABSTRACT

An artificial intelligence cloud diagnosis platform is provided. A subject sample is scanned to a cloud side, AI on the cloud conducts preliminary detection, and then a doctor carries out diagnosis and rechecking. The artificial intelligence cloud diagnosis improves the diagnosis accuracy, fundamentally solves the problems of insufficient technical experts and non-uniform medical resource distribution in remote areas, greatly improves the diagnosis efficiency, reduces the diagnosis cost, establishes a professional database of the same type of detection samples, and is beneficial to the further research of a disease in the later period.

6 Claims, 11 Drawing Sheets

(51) Int. Cl.
*G16H 10/40* (2018.01)
*G06T 7/136* (2017.01)
*G06T 7/00* (2017.01)
*G06T 7/11* (2017.01)
*G06T 7/155* (2017.01)
*G06T 7/33* (2017.01)
*G16H 15/00* (2018.01)
*G16H 30/40* (2018.01)

the cell images are scattered after software scanning images are automatically matched with relevant positions through a "visual field sub-block matching" algorithm since after the position matching is successful, the positions of the cells will be slightly deviated the positions of the cells are accurately stitched by a "visual field position fitting" algorithm

ARTIFICIAL INTELLIGENCE CLOUD DIAGNOSIS PLATFORM

FIELD

The present invention relates to the field of artificial intelligence diagnosis, in particular to an artificial intelligence cloud diagnosis platform.

BACKGROUND

China has a vast territory, but high-quality medical resources are insufficient and unevenly distributed. The pattern of the medical service system and the people's needs for medical treatment are not suitable and mismatched. Especially in rural areas, artificial diagnosis of cancer cells cannot be effectively carried out due to the lack of technical experts. With the development of artificial intelligence and big data technology, remote cloud diagnosis and remote acquisition of test reports can be achieved as long as subjects provide their test samples and upload them to the cloud side, which effectively solves the "difficulties in getting medical services" in remote areas and areas with insufficient medical resources. In the Chinese patent CN109410107A entitled "Cloud Platform System for Disease Screening", a case information screening module collects remote disease case information, a digital specialist case module forms a complete structured electronic medical record data record of various disease case information, and a remote collaborative screening module implements remote collaborative screening between networked institutions and doctors, and then realizes disease screening on the cloud. However, this patent only stores cases on the cloud, and then retrieves the data from the cloud during screening, which cannot realize the data processing on the cloud and cannot actually reduce the workload of detection personnel.

SUMMARY

The technical problem to be solved by the present invention is to provide an artificial intelligence cloud diagnosis platform, which can realize the preliminary AI diagnosis of cancer cells on the cloud, and then a doctor performs re-diagnosis and review, such that the detection accuracy is improved and the detection cost is reduced.

In order to achieve the above objective, the technical solutions used in the present invention are as follows: an artificial intelligence cloud diagnosis platform, which is implemented by the following steps:
S1: numbering subject samples to determine sample numbers in a cloud system;
S2: registration: entering subject information into the system and entering the sample numbers;
scanning: digitalizing the samples;
S3: uploading: uploading the digitalized samples to the cloud system;
S4: stitching classification: processing the digitalized samples on cloud AI;
S5: connection: associating the registration information with information of the digitalized sample in the system;
S6: diagnosis: diagnosing and reviewing the samples, and submitting a diagnosis opinion operation by a doctor; and
S7: report rendering: polling the completely diagnosed data in the system by using a rendering program and rendering the data into PDF, JPG, WORD format files according to corresponding report templates thereof; wherein auxiliary diagnosis on the cloud system is realized through the above steps.

In a preferred embodiment, the sample numbers in the cloud system are generated according to a coding rule when numbering is performed in step S1; and an original number of a subject sample is acquired by reverse decoding when the original number is needed.

In a preferred embodiment, the digitalized samples are uploaded to the cloud system after files are encrypted on a client side; thereby ensuring the safety of data.

In a preferred embodiment, in step S4, stitching a plurality of images of a single sample, and extracting according to cell nucleus features in the stitched image to acquire the microscopic images of the single cell nucleus;
classifying the microscopic images of the single cell nucleus according to the labeled cells by means of an artificial intelligence program subjected to model training;
thereby acquiring sample-based classified cell data.

In a preferred embodiment, the image stitching process comprises: visual field sub-block matching, visual field position fitting and block extraction.

The process of the visual field sub-block matching is as follows:
Sa01: inputting and initiating a result set M;
Sa02: setting the current visual field i as a first visual field;
Sa03: solving a set J of all adjacent visual fields of the current visual field i;
Sa04: setting the current adjacent visual field j as a first visual field in J;
Sa05: solving possible overlapping regions Ri and Rj of the visual field i and the visual field j;
Sa06: rasterizing a template region Ri into template sub-block sets Pi;
Sa07: sorting the template sub-block sets Pi in a descending order according to a dynamic range of the sub-blocks;
Sa08: setting the current template sub-block P as the first one in the template sub-block sets Pi;
Sa09: solving a possible overlapping region s of the template sub-block P in the visual field J;
Sa10: performing a template matching search by taking the template sub-block P as a template and s as a search region;
Sa11: adding a best match m to the result set M;
Sa12: finding all matching visual field sets N that are in consistent with m from the result set M;
Sa13: judging whether or not a weight in N is greater than a threshold v upon comparison;
if not, setting the current template sub-block P as the next one in the template sub-block sets Pi and returning to Sa09;
if yes, proceeding to next step;
Sa14: judging whether or not the visual field j is the last visual field in the visual field set J upon comparison;
if not, setting the visual field j as the next visual field in the visual field set J and returning to Sa05;
if yes, proceeding to next step;
Sa15: judging whether or not the visual field i is the last visual field upon comparison;
if not, setting i as the next visual field and returning to Sa03;
if yes, outputting a result.

In a preferred embodiment, the process of visual field position fitting is as follows:
- Sa16: inputting and initializing all visual field positions Xi, Yi;
- Sa17: setting the current visual field i as a first visual field;
- Sa18: acquiring a matching subset Mi including the visual field i from a sub-block matching set M;
- Sa19: recalculating the positions Xi and Yi of the visual field i according to the matching subset Mi;
- Sa20: judging whether or not all visual field updates are completed;
  - if not, setting the visual field i as the next visual field;
  - if yes, proceeding to next step;
- Sa21: calculating an average deviation L between the current visual field position and the previous visual field position;
- Sa22: judging whether or not the average deviation L is less than a threshold value 1 upon comparison;
  - if not, returning to Sa17;
  - if yes, proceeding to next step; and
- Sa23: performing normalized adjustment on the visual field positions; and
outputting all the visual fields.

In a preferred embodiment, the process of block extraction is as follows:
- Sa24: extracting sizes W, H of a full graph;
- Sa25: dividing the full graph into a set B of blocks according to the block sizes;
- Sa26: calculating the positions of all blocks b in the set B;
- Sa27: setting one of the blocks b as the first block in the set B;
- Sa28: calculating a set Fb of all visual fields overlapping with the block b;
- Sa29: setting a visual field f as the first visual field in Fb;
- Sa30: solving the overlapping regions Rb and Rf of the visual field f and the block b;
- Sa31: copying an image in Rf to Rb;
- Sa32: judging whether or not the visual field f is the last visual field in the set Fb;
  - if not, setting the visual field f as the next visual field in Fb and returning to Sa29;
  - if yes, proceeding to next step; and
- Sa33: saving an image of the block b;
- Sa34: judging whether or not the block b is the last block in the set B;
  - if not, setting the block b as a first block in the set B and returning to Sa28; and
  - if yes, outputting a result.

In a preferred embodiment, the process of acquiring the microscopic images of the single cell nucleus is as follows:
- Sa100: detecting features points of the cell nucleus;
  reducing the image to a plurality of different scales and extracting feature points respectively;
- Sa101: performing preliminary screening, i.e., screening to remove feature points that are too close by using coordinates of the feature points, thereby reducing repeated extraction of cells;
- Sa102: subdividing, i.e., segmenting according to a color difference threshold;
  converting a picture to a LAB format; and after the inversion of a B channel as well as the weighting and Otsu thresholding of an A channel, segmenting to acquire a cell nucleus mask map, wherein
  the weight is 0.7 for the B channel under the inversion and 0.3 for the A channel;
- S103: performing image morphology operation:
  one or a combination of more of corrosion operation and expansion operation; and
- S104: performing fine screening according to a nuclear occupancy parameter to remove non-cells each having a nuclear occupancy ratio below 0.3 and a nucleus radius above 150 pixels and below 10 pixels, wherein the nuclear occupancy ratio is obtained by dividing a nuclear area finely segmented according to the color difference threshold by a radius circle area of the detected feature point.

In a preferred embodiment, the image classification process comprises the following steps:
- St1: acquiring microscopic images;
- St2: stitching a plurality of images of a single sample, and extracting according to cell nucleus features in the stitched image to acquire the microscopic images of the single cell nucleus;
- St3: classifying the microscopic images of the single cell nucleus according to the labeled cells by means of an artificial intelligence program subjected to model training; thereby acquiring sample-based classified cell data through the above steps.

In a preferred embodiment, in step St2, the image stitching process comprises: visual field sub-block matching, visual field position fitting and block extraction;
the process of the visual field sub-block matching is as follows:
- S01: inputting and initiating a result set M;
- S02: setting the current visual field i as a first visual field;
- S03: solving a set J of all adjacent visual fields of the current visual field i;
- S04: setting the current adjacent visual field j as a first visual field in J;
- S05: solving possible overlapping regions Ri and Rj of the visual field i and the visual field j;
- S06: rasterizing a template region Ri into template sub-block sets Pi;
- S07: sorting the template sub-block sets Pi in a descending order according to a dynamic range of the sub-blocks;
- S08: setting the current template sub-block P as the first one in the template sub-block sets Pi;
- S09: solving a possible overlapping region s of the template sub-block P in the visual field J;
- S10: performing a template matching search by taking the template sub-block P as a template and s as a search region;
- S11: adding a best match m to the result set M;
- S12: finding all matching visual field sets N that are in consistent with m from the result set M;
- S13: judging whether or not a weight in N is greater than a threshold v upon comparison;
  - if not, setting the current template sub-block P as the next one in the template sub-block sets Pi and returning to S09;
  - if yes, proceeding to next step;
- S14: judging whether or not the visual field j is the last visual field in the visual field set J upon comparison;
  - if not, setting the visual field j as the next visual field in the visual field set J and returning to S05;
  - if yes, proceeding to next step;
- S15: judging whether or not the visual field i is the last visual field upon comparison;
  - if not, setting i as the next visual field and returning to S03;
  - if yes, outputting a result.

The present invention provides an artificial intelligence cloud diagnosis platform, which has the following beneficial effects by adopting the above schemes.

1. The accuracy of diagnosis is improved, and the remote cloud diagnosis method fundamentally solves the problem of insufficient technical experts and uneven distribution of medical resources in remote areas, and solves the problem of "difficulties in getting medical services" in remote areas, especially in rural areas.

2. The efficiency of diagnosis is greatly improved, and the cost of diagnosis is reduced. The number of times a subject goes to and from the hospital is reduced because remote multi-party collaborative diagnosis is realized, such that the diagnosis results are more accurate and the efficiency is higher. AI on the cloud can achieve preliminary diagnosis, which greatly reduces the cost of diagnosis.

3. A professional database of the same type of test samples is established. Cloud diagnosis can collect test samples for the same type of diseases and, relying on big data, can clearly show the distribution information of the diseases and collect information about patients, which is conducive to the further research of the diseases in the later period.

BRIEF DESCRIPTION OF THE DRAWINGS

The present invention will be further described below in conjunction with the accompanying drawings and embodiments.

DETAILED DESCRIPTION

Embodiment 1

Figure 1:
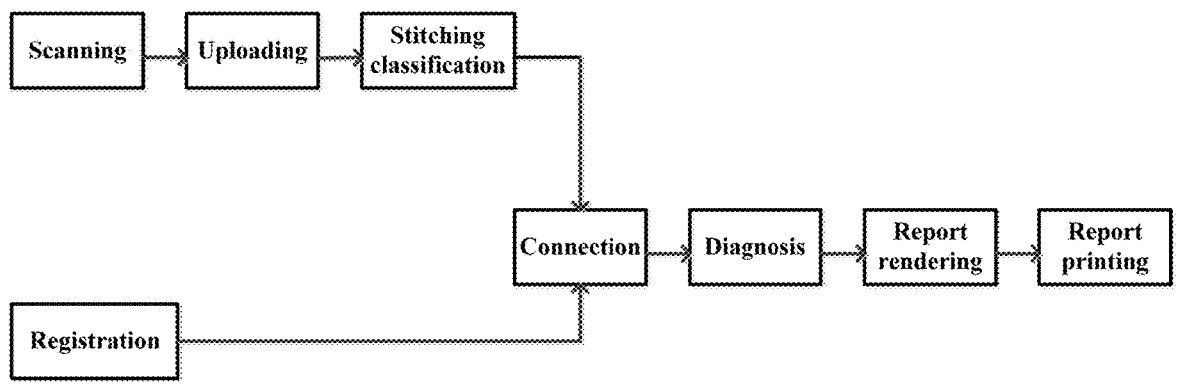
FIG. 1 is a flowchart of cloud diagnosis in the present invention.

As shown in FIG. 1, an artificial intelligence cloud diagnosis platform is implemented as follows.

S1: numbering subject samples to determine sample numbers in a cloud system. The subject samples are acquired before the process on the cloud starts. After a batch of samples are acquired uniformly, they will be renumbered to determine a correspondence between the samples and information of subjects.

S2: registration: entering the information of the subjects into the system and entering the sample numbers; and scanning: digitalizing the samples. Registration and scanning are performed at the same time without interference. In the course of registering, the information of the subjects is entered into the system, and the renumbered sample numbers are entered.

S3: uploading: uploading the digitalized samples to the cloud system. The cloud system provides a network-based data access service, which can store and call various unstructured data files including text, pictures, audio, video and the like at any time through a network. Alibaba Cloud OSS uploads data files into a bucket in a form of objects, which have rich SDK packages and adapt to different computer languages for secondary development.

S4: stitching classification: processing the digitalized samples on cloud AI. The cloud AI performs a preliminary diagnosis on the digitized subject samples, and the subject samples at risk of disease are passed to step S6 for further diagnosis by the doctor.

S5: connection: associating the registration information with the digitalized sample information in the system. Associating the personal information of the subject with the sample information of the subject is convenient for feeding an inspection report back to the subject at the later stage, which is beneficial to the later collation and further research of the data at the same time.

S6: diagnosis: diagnosing and reviewing the samples, and submitting a diagnosis opinion operation by a doctor. The subject report who may have a risk of disease in the preliminary diagnosis by AI is diagnosed and reviewed by the doctor, which improves the accuracy of the diagnosis but greatly reduces the cost of diagnosis. A sampling mechanism completes the acquisition of cell specimen image information, and then passes the data to the cloud diagnosis platform via the Internet. The artificial intelligence will automatically complete the diagnosis, and the doctor only needs to review and confirm the results that are positive. Because positive cases are often in the minority, artificial intelligence cloud diagnosis can save a lot of manual labor.

S7: report rendering: polling the completely diagnosed data in the system by using a rendering program and rendering the data into PDF, JPG, WORD format files according to corresponding report templates thereof. The rendering program is used to render a web page according to the required report template, extract required fields, call PDF, JPG, and WORD components, and generate PDF, JPG, and WORD format files. Reports may also be printed. The corresponding programs can be connected to a printer to print the reports in batches. The hospital can call a local printer driver through a system web interface, and print the reports in batches as needed. At the same time, the system can feed an electronic report back to the subject based on the entered information.

Embodiment 2

Figure 2:
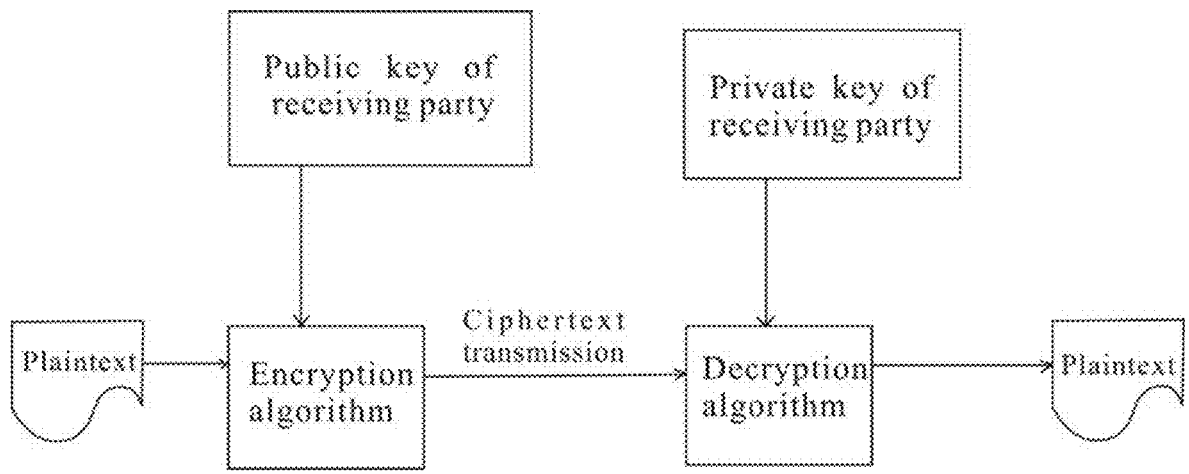
FIG. 2 is a flowchart of sample data encryption in the present invention.

As shown in FIG. 2, based on Embodiment 1, the sample numbers in the cloud system are generated according to a coding rule when numbering is performed in step S1. For example, a specific prefix is added to the front of the collected sample data number to indicate geographic information of the subject sample, such as a province, a city and a hospital, and simple personal information such as a gender and an age. When a data sample is relatively large, the subject samples can be quickly classified, and can also be quickly extracted according to the prefix information. An original number of a subject sample is acquired by reverse decoding when the original number is needed, which is convenient for the conversion between the sample numbers in the cloud system and numbers in the hospital system, thereby facilitating management and avoiding errors.

Embodiment 3

Figure 3:
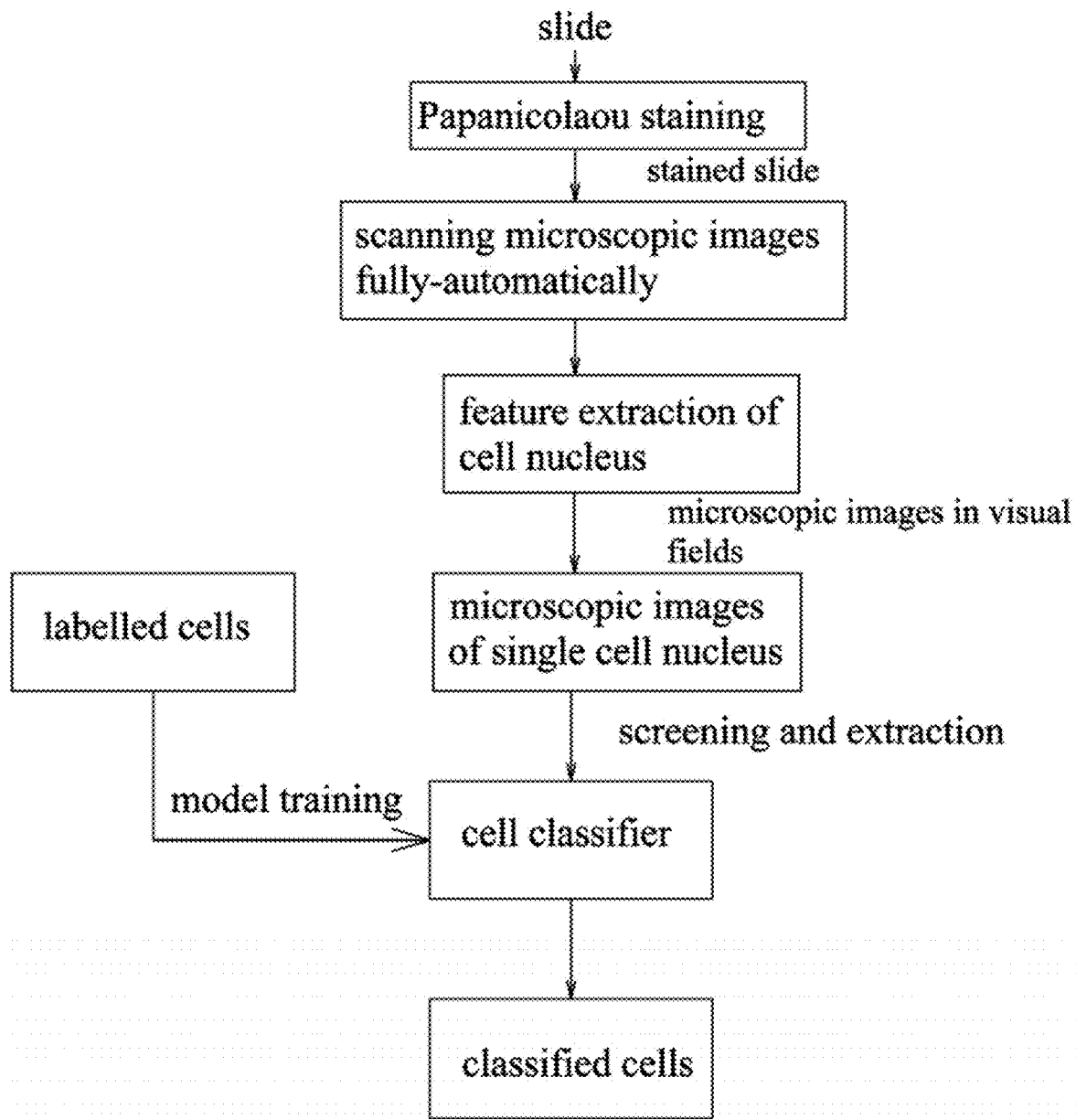
FIG. 3 is an overall schematic flowchart of the present invention.
Figure 4:
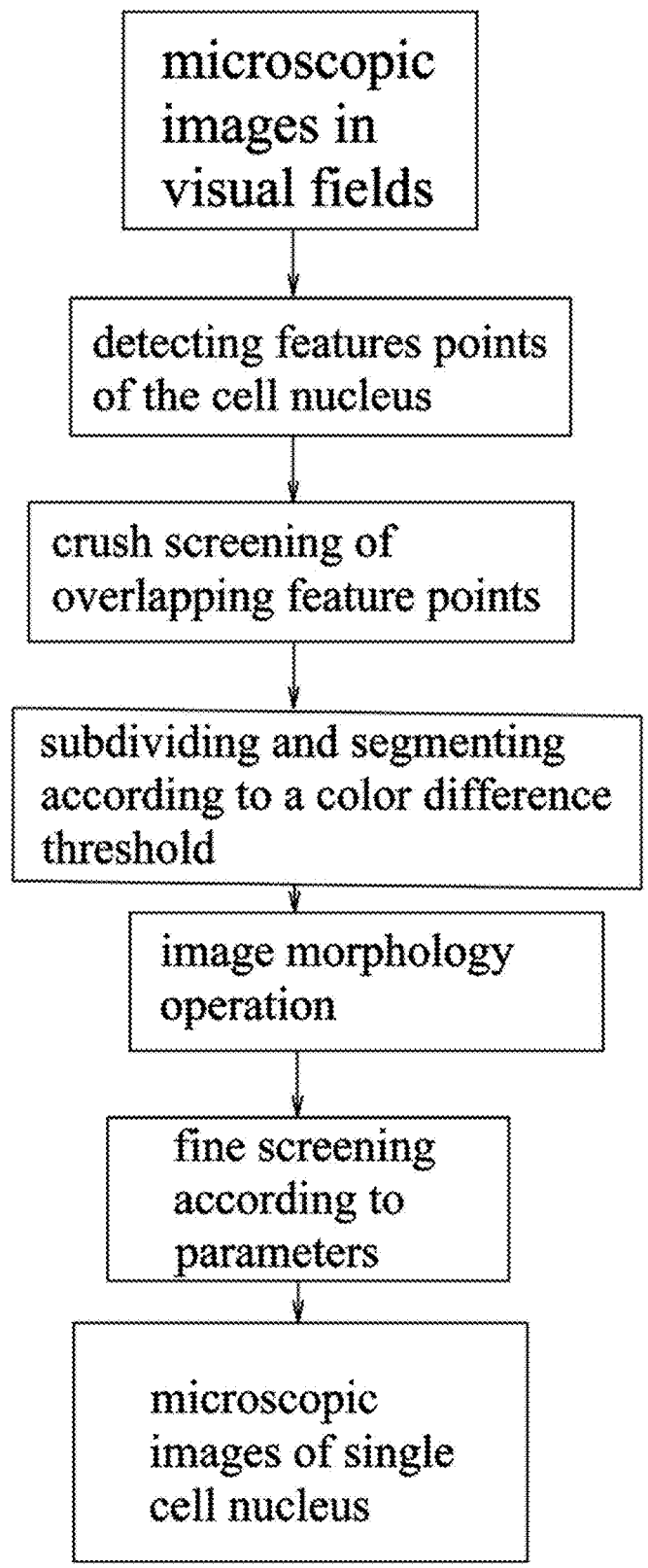
FIG. 4 is a schematic flowchart of a process of acquiring microscopic images of a single cell nucleus in the present invention.
Figure 5:
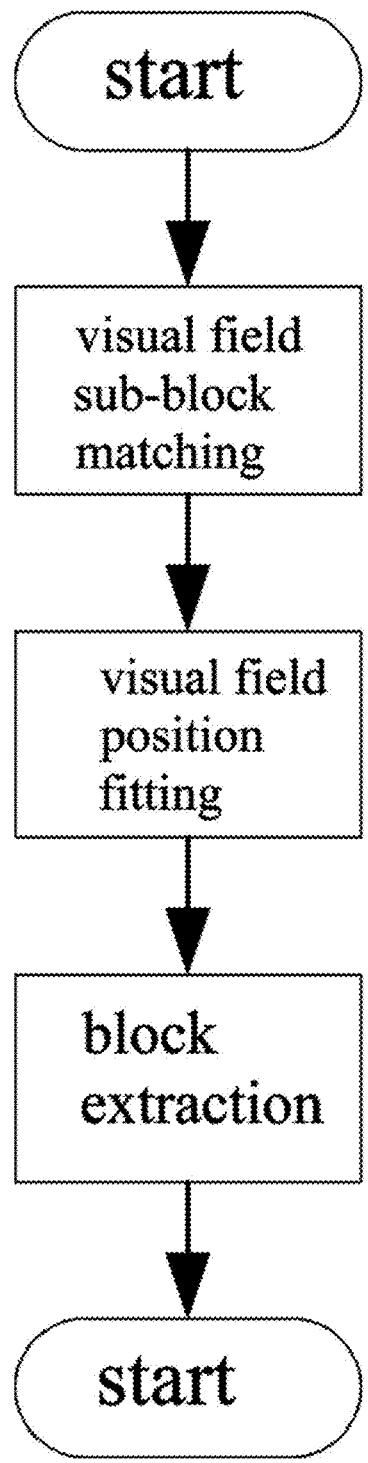
FIG. 5 is a schematic flowchart of the image recognition process in the present invention.

As shown in FIG. 3, the digitized samples are uploaded to the cloud system after files are encrypted on a client side. As a third-party cloud storage service product, the cloud system provides a data security protection function, but the data encryption is accomplished by a cloud storage service provider, which is capable of preventing attacks from ordinary users, but is still transparent to insiders of a cloud service system. For medical information, especially information that may involve genetic resources such as cytology, once leaked, it will have a greater impact on the country and the people. In order to ensure the security of medical data in the cloud diagnosis process, in step S3, the digitalized samples are uploaded to the cloud system after the files are encrypted on the client side. A data key is a temporary key, i.e., a private key, applied by an uploader to the system. The encrypted data sample does not affect the processing of the sample data by the AI cloud system. When a report is exported, a public key in keys is used for identity verification and decryption, and then the information is exported. Considering that the sample data encryption is time-consuming, a new thread may be opened for data encryption. A master key and an initial vector of the master key encrypt a file key and an initial vector of the file key so as to acquire a file key ciphertext. Then, the initial vector of the master key and the file key ciphertext are spliced into a character string as a file header. During decryption, after the data is acquired, the file header composed of the keys is extracted first, the initial vector of the master key and the file key ciphertext are separated out, and the master key and the initial vector of the master key are used to decrypt to acquire the file key and the initial vector of the file key, which are used to decrypt a file. Therefore, a new thread is also opened for decryption.

Embodiment 4

Figure 12A:
FIG. 12a is a schematic diagram of an operation flow of visual field position fitting in the present invention.
Figure 12A:
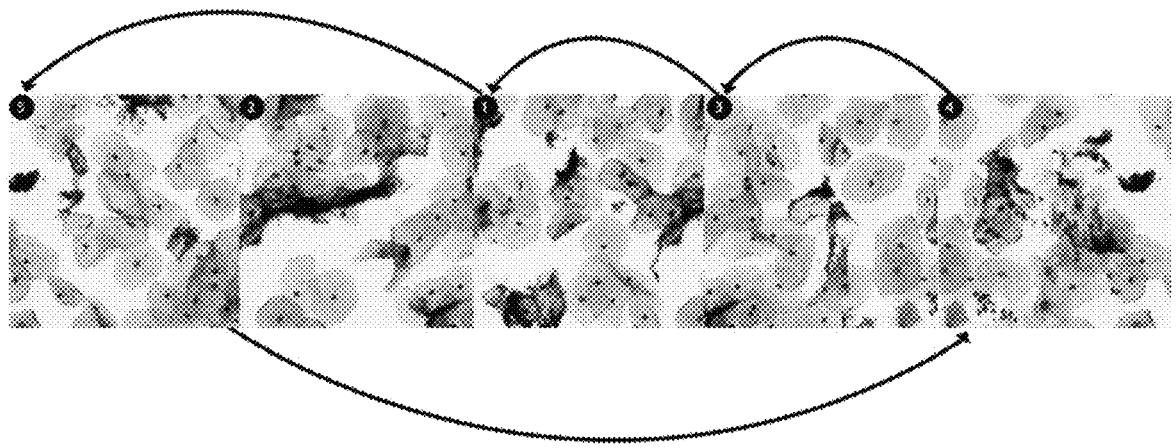
Figure 12B:
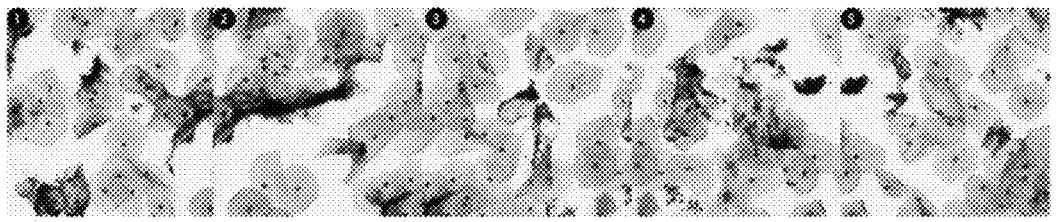
FIG. 12b is a schematic flowchart of an operation flow of visual field sub-block matching in the present invention.
Figure 12B:
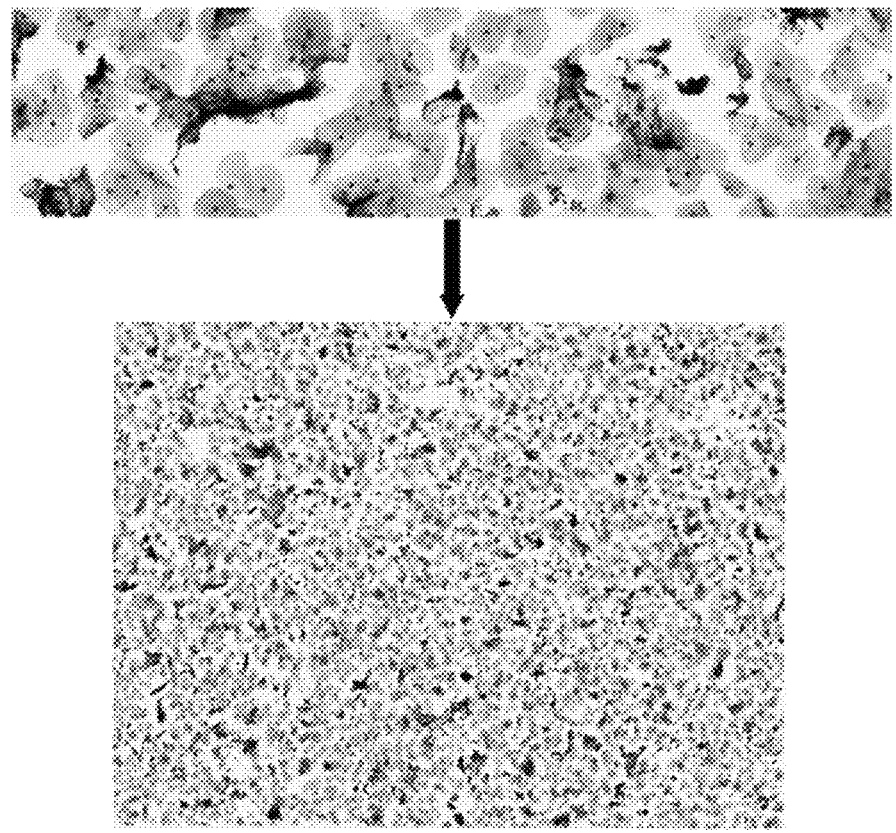

As shown in FIGS. 3-8, in step S4, a plurality of images of a single sample is stitched by the AI cloud system. As shown in FIG. 12a and FIG. 12b, the microscopic images of the single cell nucleus are acquired by extracting according to cell nucleus features in the stitched image.

The microscopic images of the single cell nucleus are classified according to the labeled cells by means of an artificial intelligence program subjected to model training.

Figure 10:
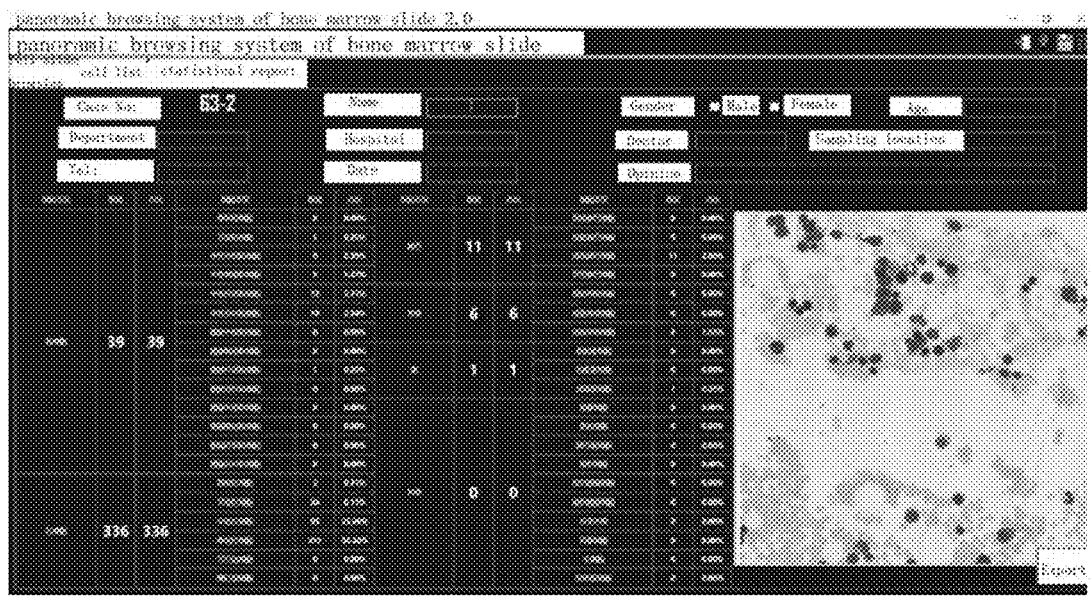
FIG. 10 is an example diagram of a cell classification process in the present invention.

As shown in FIG. 10, the artificial intelligence program preferably uses a convolutional neural network with a learning rate of 0.001. The number of result categories is num_classes=3, which corresponds to positive, negative, and garbage respectively. The number of training rounds: epochs=300; image size: img_cols=128 img_rows=128; regular parameter: reg=0.7; the number of consecutive declines: patience=10.

Therefore, the target-based classified cell data are acquired.

Embodiment 5

Based on Embodiment 4, a preferred solution is shown in in FIGS. 5-8. The image stitching process comprises: visual field sub-block matching, visual field position fitting and block extraction.

Figure 6:
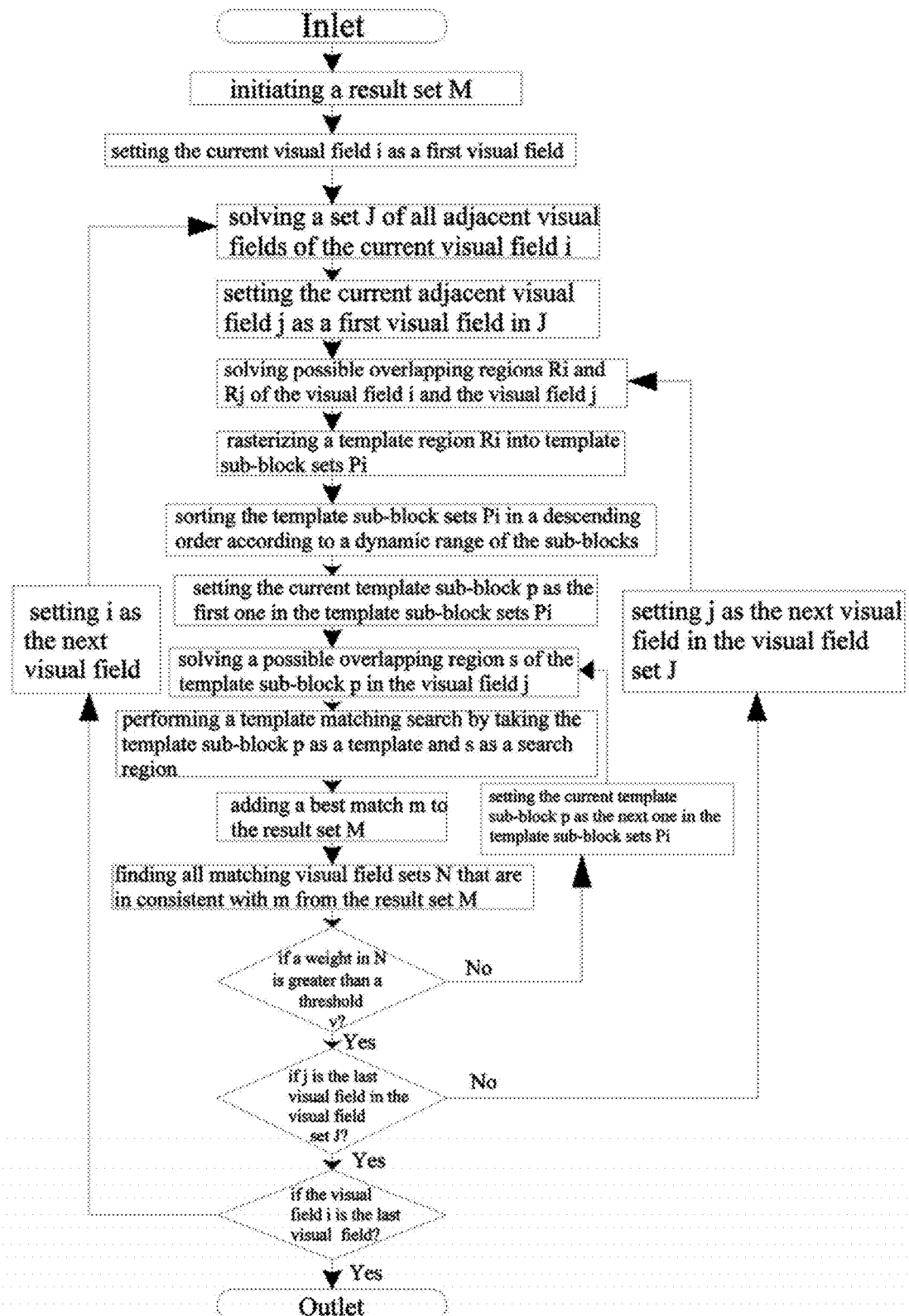
FIG. 6 is a schematic flowchart of visual field sub-block matching in the present invention.

As shown in FIG. 6 and FIG. 12a, the process of the visual field sub-block matching is as follows:
Sa01: inputting and initiating a result set M;
Sa02: setting the current visual field i as a first visual field;
Sa03: solving a set J of all adjacent visual fields of the current visual field i;
Sa04: setting the current adjacent visual field j as a first visual field in J;
Sa05: solving possible overlapping regions Ri and Rj of the visual field i and the visual field j;
Sa06: rasterizing a template region Ri into template sub-block sets Pi;
Sa07: sorting the template sub-block sets Pi in a descending order according to a dynamic range of the sub-blocks;
Sa08: setting the current template sub-block P as the first one in the template sub-block sets Pi;
Sa09: solving a possible overlapping region s of the template sub-block P in the visual field J;
Sa10: performing a template matching search by taking the template sub-block P as a template and s as a search region;
Sa11: adding a best match m to the result set M;
Sa12: finding all matching visual field sets N that are in consistent with m from the result set M;
Sa13: judging whether or not a weight in N is greater than a threshold v upon comparison;
if not, setting the current template sub-block P as the next one in the template sub-block sets Pi and returning to Sa09;
if yes, proceeding to next step;
Sa14: judging whether or not the visual field j is the last visual field in the visual field set J upon comparison;
if not, setting the visual field j as the next visual field in the visual field set J and returning to Sa05;
if yes, proceeding to next step;
Sa15: judging whether or not the visual field i is the last visual field upon comparison;
if not, setting i as the next visual field and returning to Sa03;
if yes, outputting a result; Through such solution, an adjacent positional relationship between the sub-images is determined by intelligently recognizing an overlapping region between every two adjacent images, so that the sub-images acquired by a microscopic scanning device are automatically arranged in a stitching order of the images.

Figure 7:
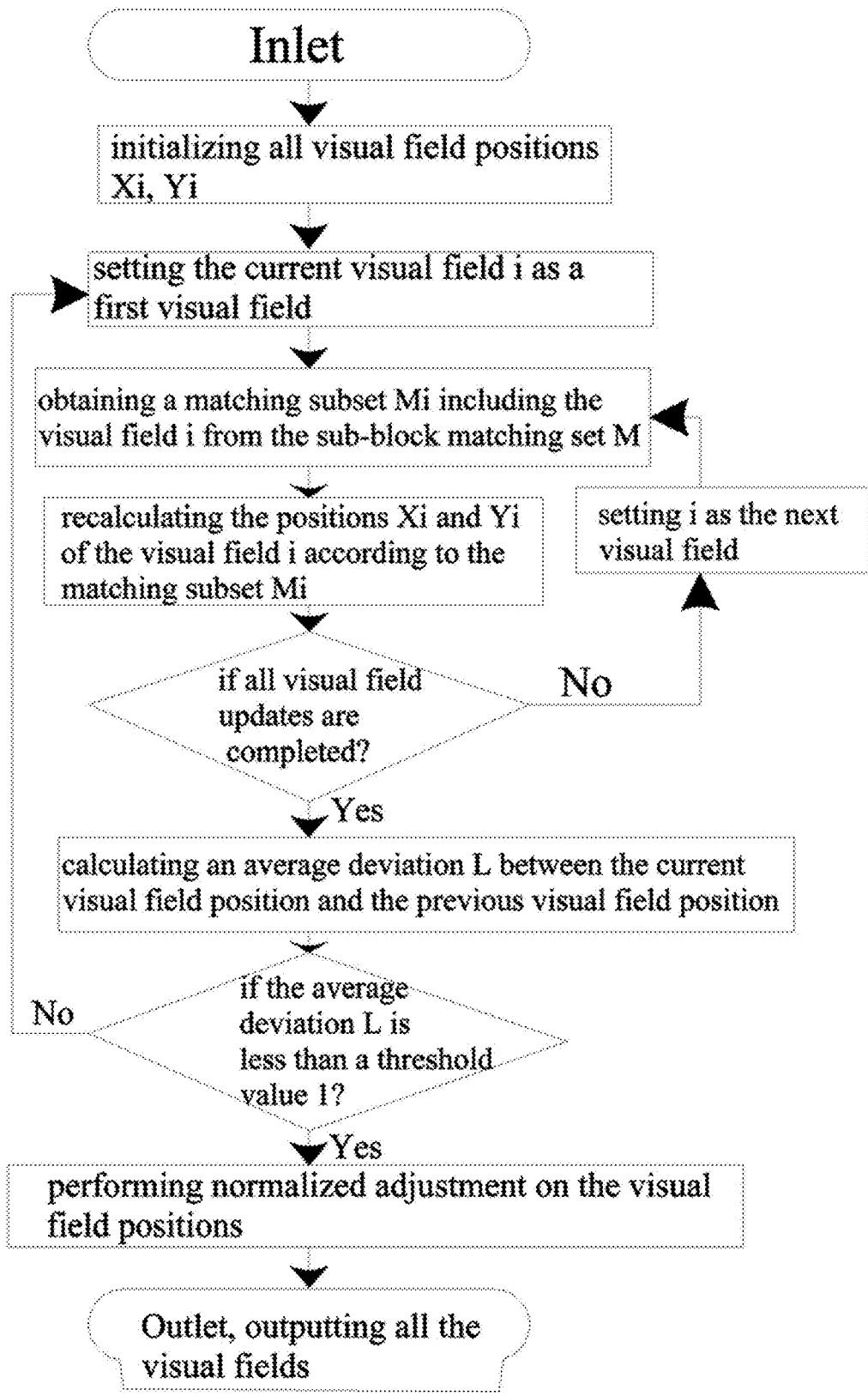
FIG. 7 is a schematic flowchart of visual field position fitting in the present invention.

A preferred solution is shown in in FIGS. 7 and 12b, the process of visual field position fitting is as follows:
Sa16: inputting and initializing all visual field positions Xi, Yi;
Sa17: setting the current visual field i as a first visual field;
Sa18: acquiring a matching subset Mi including the visual field i from a sub-block matching set M;
Sa19: recalculating the positions Xi and Yi of the visual field i according to the matching subset Mi;
Sa20: judging whether or not all visual field updates are completed;
if not, setting the visual field i as the next visual field;
if yes, proceeding to next step;
Sa21: calculating an average deviation L between the current visual field position and the previous visual field position;

Sa22: judging whether or not the average deviation L is less than a threshold value 1 upon comparison;
if not, returning to Sa17;
if yes, proceeding to next step; and
Sa23: performing normalized adjustment on the visual field positions; and
outputting all the visual fields.

Figure 8:
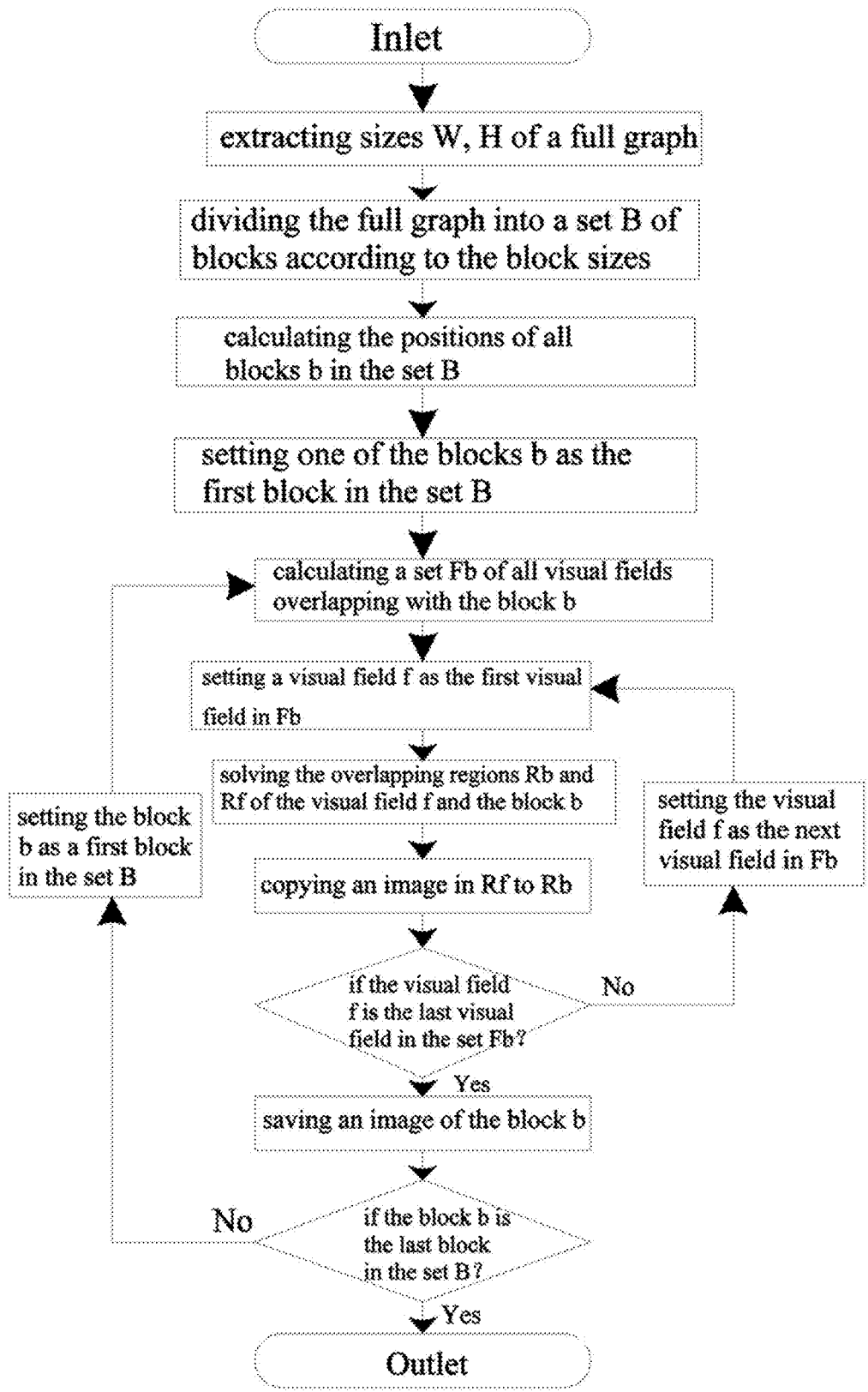
FIG. 8 is a schematic flowchart of block extraction in the present invention.

A preferred solution is shown in in FIG. 8, the process of block extraction is as follows:
Sa24: extracting sizes W, H of a full graph;
Sa25: dividing the full graph into a set B of blocks according to the block sizes;
Sa26: calculating the positions of all blocks b in the set B;
Sa27: setting one of the blocks b as the first block in the set B;
Sa28: calculating a set Fb of all visual fields overlapping with the block b;
Sa29: setting a visual field f as the first visual field in Fb;
Sa30: solving the overlapping regions Rb and Rf of the visual field f and the block b;
Sa31: copying an image in Rf to Rb;
Sa32: judging whether or not the visual field f is the last visual field in the set Fb;
if not, setting the visual field f as the next visual field in Fb and returning to Sa29;
if yes, proceeding to next step; and
Sa33: saving an image of the block b;
Sa34: judging whether or not the block b is the last block in the set B;
if not, setting the block b as a first block in the set B and returning to Sa28; and if yes, outputting a result. By means of such solution, positions are finely tuned according to the overlapping region between every two adjacent sub-images, so that cell positions are accurately stitched.

Embodiment 6

Based on Embodiments 4-5, the preferred solution is shown in FIG. 4, and FIGS. 9-11. The process of acquiring the microscopic images of the single cell nucleus is as follows:
Sa100: detecting features points of the cell nucleus;
reducing each image to a plurality of different scales, preferably the reducing scales being 0.3, 0.15, and 0.08; extracting feature points respectively;
Sa101: performing preliminary screening, i.e., screening to remove feature points that are too close by using coordinates of the feature points, thereby reducing repeated extraction of cells. By means of this step, the efficiency of recognition is greatly improved.
It is set in this embodiment: if the distance between the feature points is not more than half of the radius of a cell, and the half of the radius is greater than 32, it is considered that the feature points are too close if the distance is less than 32 pixels, otherwise it is considered that the feature points are too close if the distance is less than half of the radius of the cell. That is, cell.Center.L1DistanceTo(d.Center)<Math.Min(cell.Radius*0.5, 32).
Sa102: subdividing, i.e., segmenting according to a color difference threshold.
A picture is converted to a LAB format, which, after the inversion of a B channel as well as the weighting and Otsu thresholding of an A channel, is segmented to acquire a cell nucleus mask map. In the prior art, gray values are used for screening. However, according to the form of gray value, because gray usually has only one channel, and has a range from 1 to 255 only, it is difficult to distinguish for some subtle positions. However, the combined solution of B channel and A channel has two channels, which can greatly increase the value range and improve the screening accuracy.

Figure 9:
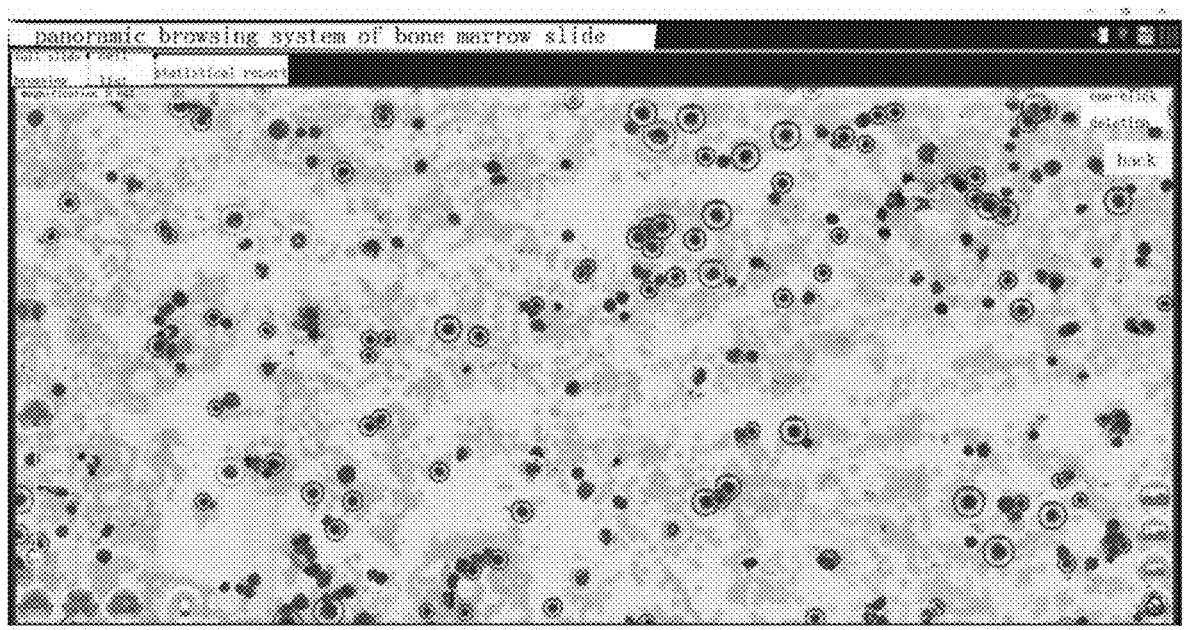
FIG. 9 is an example diagram after image recognition in the present invention.

The weight is 0.7 for the B channel under the inversion and 0.3 for the A channel.
Sa103: performing image morphology operation:
a combination of one or more of corrosion operation and expansion operation. The corrosion calculation and expansion calculation are, for example, calculation methods in the Chinese patent document CN106875404A.
Sa104: performing fine screening according to a nuclear occupancy parameter to remove non-cells each having a nuclear occupancy ratio below 0.3 and a nucleus radius above 150 pixels and below 10 pixels, wherein the nuclear occupancy ratio is obtained by dividing a nuclear area finely segmented according to the color difference threshold by a radius circle area of the detected feature point. The results are shown in FIG. 9. The recognized images of the feature cells of the user are clearly displayed to facilitate the doctor's diagnosis.

Embodiment 7

Based on Embodiments 4-6, the preferred solution is shown in FIGS. 3-8, it comprises the following steps:
St1: acquiring microscopic images;
St2: stitching a plurality of images of a single sample, and extracting according to cell nucleus features in the stitched image to acquire the microscopic images of the single cell nucleus;
St3: classifying the microscopic images of the single cell nucleus according to the labeled cells by means of an artificial intelligence program subjected to model training; thereby acquiring sample-based classified cell data through the above steps.

In a preferred solution, in the Step St2, the image stitching process comprises: visual field sub-block matching, visual field position fitting and block extraction; the process of the visual field sub-block matching is as follows:
S01: inputting and initiating a result set M;
S02: setting the current visual field i as a first visual field;
S03: solving a set J of all adjacent visual fields of the current visual field i;
S04: setting the current adjacent visual field j as a first visual field in J;
S05: solving possible overlapping regions Ri and Rj of the visual field i and the visual field j;
S06: rasterizing a template region Ri into template sub-block sets Pi;
S07: sorting the template sub-block sets Pi in a descending order according to a dynamic range of the sub-blocks;
S08: setting the current template sub-block P as the first one in the template sub-block sets Pi;
S09: solving a possible overlapping region s of the template sub-block P in the visual field J;
S10: performing a template matching search by taking the template sub-block P as a template and s as a search region;
S11: adding a best match m to the result set M;
S12: finding all matching visual field sets N that are in consistent with m from the result set M;

S13: judging whether or not a weight in N is greater than a threshold v upon comparison;

if not, setting the current template sub-block P as the next one in the template sub-block sets Pi and returning to S09;

if yes, proceeding to next step;

S14: judging whether or not the visual field j is the last visual field in the visual field set J upon comparison;

if not, setting the visual field j as the next visual field in the visual field set J and returning to S05;

if yes, proceeding to next step;

S15: judging whether or not the visual field i is the last visual field upon comparison;

if not, setting i as the next visual field and returning to S03;

if yes, outputting a result.

Embodiment 8

Based on Embodiments 4-7, in FIGS. 9-12, a case of a cell pathology analysis is taken as an example: an image automatically acquired from the microscopic scanning device is shown in the upper image of FIG. 12a, and various sub-images are ordered irregularly, which depends on an automatic acquisition path of the microscopic scanning device. During the acquisition process, it is necessary to ensure that there are mutually overlapping positions between every two of the images. The pixel values of the overlapping positions are analyzed. The images are automatically matched with the corresponding positions by means of a visual field sub-block matching intelligent algorithm. An initial value of a two-dimensional transformation matrix from a platform offset to a pixel offset is calculated according to the matching feature points in the adjacent virtual fields, thereby acquiring stitching parameters. Specifically, each visual field sub-block is determined, that is, the adjacent positions of the sub-image relative to other sub-images are determined. A common part between the adjacent visual fields is cut into a plurality of small blocks, common coincident regions are found by using template matching, and matching blocks with a matching threshold greater than 0.9 are selected. The correlation of template matching for all visual fields is calculated. As shown in FIG. 12b, after the position matching is successful, the positions of the respective cells will be slightly deviated, and the positions of the cells are accurately stitched by a visual field position fitting intelligent algorithm. Specifically, after template matching, the approximate positions of pixels in each visual field can be acquired. The maximum pixel deviation is calculated according to initial stitching parameters and a maximum displacement deviation of the platform. The points where each visual field has a matching relationship with the neighboring visual field are filtered by using the maximum pixel deviation, so as to remove points the deviation of which is greater than the maximum pixel deviation. The stitching parameters are recalculated according to the screened points. The pixel positions of the visual fields are recalculated by using the latest stitching parameters. Through continuous iterative filtering and recalculation, the picture position in each visual field can be continuously updated and improved, so that the error is smaller and the stitching effect is more perfect. After the picture position in each visual field is calculated, the brightness of each visual field is updated through a background image by using a calculation background during the scanning process, thereby improving the doctor's visual perception to view each visual field. A perfect slide picture can be obtained by stitching, and the entire stitched image may be extracted as one block. Then, according to the needs, the big picture is cut to acquire the pictures with the desired widths and heights, because the big picture stitched by all visual fields will be large and unnecessary.

Figure 11:
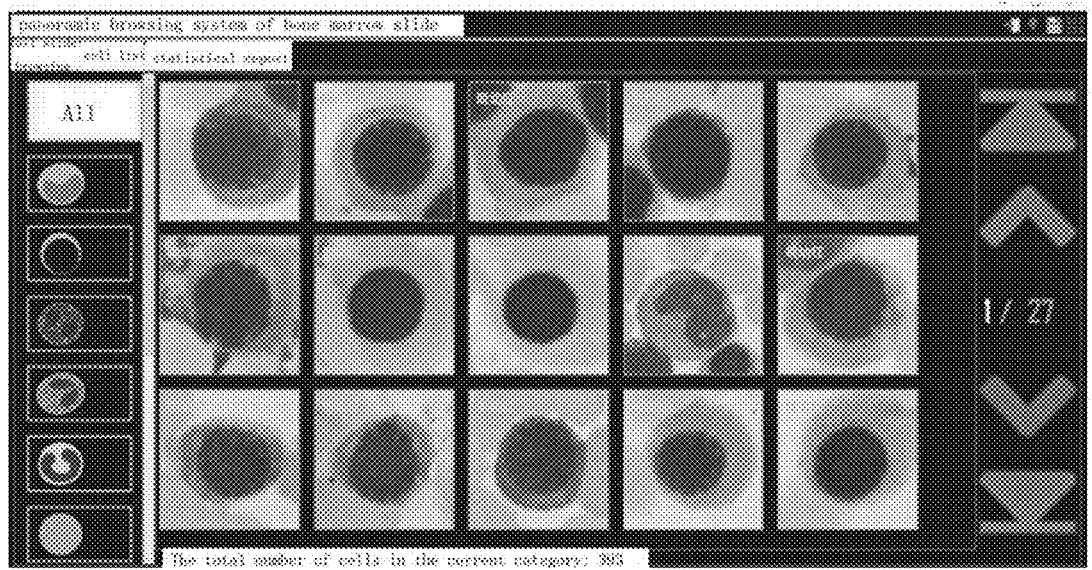
FIG. 11 is a feature morphology diagram of a single cell nucleus capable of characterizing the user's cytopathology acquired in the present invention.

As shown in FIG. 9, feature points of a cell nucleus are detected. That is, the feature points of the cell nucleus are detected by a SURF algorithm. The image is reduced to different scales, and the feature points are extracted respectively. Preliminary screening is performed, i.e., feature points that are too close are removed by screening by using coordinates of the feature points, to reduce repeated extraction of cells, that is, only one of cells with the same feature points remains. Through this step, the efficiency of recognition is greatly improved. Subdividing is performed, i.e., segmenting according to a color difference threshold. Compared with gray-level threshold segmentation, the color-difference threshold segmentation scheme can greatly improve the accuracy of subdivision. As shown in FIG. 12b, in the case where cells overlap each other, it can be seen that the color change of the image is greatly different, resulting in easy recognition. When FIG. 12b is converted to a grayscale image, the difficulty of resolution is greatly increased. Image morphology operation is performed, wherein a combination of one or more of corrosion operation and expansion operation is used; and the corrosion calculation and expansion calculation are, for example, calculation methods in the Chinese patent document CN106875404A. The erosion operation refers to corroding to remove the edges of the image, and aims to remove "burrs" on the edges of a target. The expansion operation refers to expanding the edges of the image, and aims to fill pits on the edges or inside of the target image. The target image is made to be smoother by using the same number of times of corrosion and expansion. The details are shown in FIG. 10. Fine screening is performed according to the nuclear occupancy parameter to remove non-cells with a nuclear occupancy ratio below 0.3 and a nucleus radius above 150 pixels and below 10 pixels, wherein the nuclear occupancy ratio is obtained by dividing a nuclear area finely segmented according to the color difference threshold by a radius circle area of the detected feature point. The results are shown in FIG. 11, and the recognized images of each feature cell of the user are clearly displayed in a list, and preferably, are arranged in a positive-negative order to facilitate the doctor's diagnosis and assist the doctor to improve the diagnosis efficiency. Further preferably, during the operation, the coordinates of diagonal points of the resulting feature cell image are retained. For example, during the operation process, a coordinate operation record is retained in a form of a log, and the coordinate position of the feature cell image on the stitched image is retained so that the doctor can quickly browse the original image according to the coordinate position. Further preferably, unprocessed original sub-images can be quickly browsed according to the correspondence between the coordinates and the sub-images to prevent important cytopathological image features from being erased by intelligent operations and further determine the diagnostic accuracy.

The above-mentioned embodiments are only preferred technical solutions of the present invention, and should not be regarded as a limitation of the present invention. The embodiments in this application and the features in the embodiments can be combined with each other arbitrarily without conflict. The protection scope of the present invention should be based on the technical solutions described in the claims, including equivalent replacement solutions of the technical features in the technical solutions described in the claims. Thus, any equivalent replacements within this scope shall be encompassed by the protection scope of the present invention.

What is claimed is:

1. A method for an artificial intelligence cloud diagnosis platform, which comprising the following steps:
S1, numbering subject samples to determine sample numbers in a cloud system;
S2, registering so as to enter subject information into the system and enter the sample numbers;
scanning so as to digitalize the samples;
S3, uploading so as to upload the digitalized samples to the cloud system;
S4, stitching classification so as to process the digitalized samples on cloud AI;
S5, connecting so as to associate registration information with information of the digitalized sample in the system;
S6, diagnosing so as to diagnose and review the samples, and submit a diagnosis opinion operation by a doctor; and
S7, report rendering so as to poll the completely diagnosed data in the system by using a rendering program and rendering the data into PDF, JPG, WORD format files according to corresponding report templates thereof; wherein
auxiliary diagnosis on the cloud system is realized through above steps;
in step S4, a plurality of images of a single sample are stitched, wherein an image stitching process comprises: visual field sub-block matching, visual field position fitting and block extraction;
a process of the visual field sub-block matching is as follows:
Sa01, inputting and initiating a result set M;
Sa02, setting the current visual field i as a first visual field;
Sa03, solving a set J of all adjacent visual fields of the current visual field i;
Sa04, setting the current adjacent visual field j as a first visual field in J;
Sa05, solving possible overlapping regions Ri and Rj of the visual field i and the visual field j;
Sa06, rasterizing a template region Ri into template sub-block sets Pi;
Sa07, sorting the template sub-block sets Pi in a descending order according to a dynamic range of the sub-blocks;
Sa08, setting the current template sub-block P as the first one in the template sub-block sets Pi;
Sa09, solving a possible overlapping region s of the template sub-block P in the visual field J;
Sa10, performing a template matching search by taking the template sub-block P as a template and s as a search region;
Sa11, adding a best match m to the result set M;
Sa12, finding all matching visual field sets N that are in consistent with m from the result set M;
Sa13, judging whether or not a weight in N is greater than a threshold v upon comparison;
if not, setting the current template sub-block P as the next one in the template sub-block sets Pi and returning to Sa09;
if yes, proceeding to next step;
Sa14, judging whether or not the visual field j is the last visual field in the visual field set J upon comparison;
if not, setting the visual field j as the next visual field in the visual field set J and returning to Sa05;
if yes, proceeding to next step;
Sa15, judging whether or not the visual field i is the last visual field upon comparison;
if not, setting i as the next visual field and returning to Sa03;
if yes, outputting a result;
after the image stitching is completed by above steps, the stitched image is extracted according to features of a cell nucleus to acquire the microscopic images of the single cell nucleus;
a process of acquiring the microscopic images of the single cell nucleus is as follows:
Sa100, detecting features points of the cell nucleus;
reducing the image to a plurality of different scales and extracting feature points respectively;
Sa101, performing preliminary screening so as to screen to remove feature points that are too close by using coordinates of the feature points, thereby reducing repeated extraction of cells;
Sa102, subdividing so as to segment according to a color difference threshold;
converting a picture to a LAB format; and after an inversion of a B channel as well as the weighting and Otsu thresholding of an A channel, segmenting to acquire a cell nucleus mask map, wherein
the weight is 0.7 for the B channel under the inversion and 0.3 for the A channel;
S103, performing image morphology operation:
one or a combination of more of corrosion operation and expansion operation; and
S104, performing fine screening according to a nuclear occupancy parameter to remove non-cells each having a nuclear occupancy ratio below 0.3 and a nucleus radius above 150 pixels and below 10 pixels, wherein the nuclear occupancy ratio is obtained by dividing a nuclear area finely segmented according to the color difference threshold by a radius circle area of the detected feature point; and
after the microscopic images of the single cell nucleus are acquired by the above steps, the microscopic images of the single cell nucleus are classified according to the labeled cells by means of an artificial intelligence program subjected to model training;
thereby obtaining target-based classified cell data.

2. The method according to claim 1, wherein the sample numbers in the cloud system are generated according to a coding rule when numbering is performed in step S1; and
an original number of a subject sample is acquired by reverse decoding when the original number is needed.

3. The method according to claim 1, wherein the digitalized samples are uploaded to the cloud system after files are encrypted on a client side, in order to ensure safety of data.

4. The method according to claim 1, wherein a process of visual field position fitting is as follows:
Sa16, inputting and initializing all visual field positions Xi, Yi;
Sa17, setting current visual field i as a first visual field;
Sa18, acquiring a matching subset Mi including the visual field i from a sub-block matching set M;
Sa19, recalculating the positions Xi and Yi of the visual field i according to the matching subset Mi;

Sa20, judging whether or not all visual field updates are completed;
if not, setting the visual field i as the next visual field;
if yes, proceeding to next step;
Sa21, calculating an average deviation L between the current visual field position and the previous visual field position;
Sa22, judging whether or not the average deviation L is less than a threshold value 1 upon comparison;
if not, returning to Sa17;
if yes, proceeding to next step; and
Sa23, performing normalized adjustment on the visual field positions; and
outputting all the visual fields.

5. The method according to claim 1, wherein,
a process of block extraction is as follows:
Sa24, extracting sizes W, H of a full graph;
Sa25, dividing the full graph into a set B of blocks according to the block sizes;
Sa26, calculating the positions of all blocks b in the set B;
Sa27, setting one of the blocks b as the first block in the set B;
Sa28, calculating a set Fb of all visual fields overlapping with the block b;
Sa29, setting a visual field f as the first visual field in Fb;
Sa30, solving the overlapping regions Rb and Rf of the visual field f and the block b;
Sa31, copying an image in Rf to Rb;
Sa32, judging whether or not the visual field f is the last visual field in the set Fb;
if not, setting the visual field f as the next visual field in Fb and returning to Sa29;
if yes, proceeding to next step; and
Sa33, saving an image of the block b;
Sa34, judging whether or not the block b is the last block in the set B;
if not, setting the block b as a first block in the set B and returning to Sa28; and
if yes, outputting a result.

6. The method according to claim 1, wherein the image classification process comprises the following steps:
St1, acquiring microscopic images;
St2, stitching a plurality of images of a single sample, and extracting according to cell nucleus features in the stitched image to acquire the microscopic images of the single cell nucleus;
St3, classifying the microscopic images of the single cell nucleus according to the labeled cells by means of an artificial intelligence program subjected to model training, in order to acquire sample-based classified cell data.

* * * * *